(12) United States Patent
Dachaud et al.

(10) Patent No.: US 12,024,702 B2
(45) Date of Patent: Jul. 2, 2024

(54) METHOD AND DEVICE FOR PREPARING SAMPLES

(71) Applicant: BIOMÉRIEUX, Marcy l'Etoile (FR)

(72) Inventors: Fabien Dachaud, Oye-et-Pallet (FR); Jacques Dachaud, Besancon (FR); Frédéric Foucault, Marcy l'Etoile (FR); Edgar Minassian, Lentilly (FR); David Mosticone, Sainte Consorce (FR); Jean-Claude Raymond, Bessenay (FR)

(73) Assignee: BIOMERIEUX, Marcy l'Etoile (FR)

( * ) Notice: Subject to any disclaimer, the term of this patent is extended or adjusted under 35 U.S.C. 154(b) by 1301 days.

(21) Appl. No.: 16/336,441

(22) PCT Filed: Oct. 9, 2017

(86) PCT No.: PCT/FR2017/052755
§ 371 (c)(1),
(2) Date: Mar. 25, 2019

(87) PCT Pub. No.: WO2018/069612
PCT Pub. Date: Apr. 19, 2018

(65) Prior Publication Data
US 2020/0024569 A1 Jan. 23, 2020

(30) Foreign Application Priority Data

Oct. 10, 2016 (FR) ........................................ 1659745
Oct. 10, 2016 (FR) ........................................ 1659746

(51) Int. Cl.
*C12M 3/00* (2006.01)
*B01L 3/00* (2006.01)
(Continued)

(52) U.S. Cl.
CPC ............ *C12M 47/04* (2013.01); *C12M 23/14* (2013.01); *C12M 23/26* (2013.01); *C12M 47/10* (2013.01);
(Continued)

(58) Field of Classification Search
CPC .............................. C12M 23/44; C12M 47/02
See application file for complete search history.

(56) References Cited

U.S. PATENT DOCUMENTS 3,963,355 A * 6/1976 Aldridge, Jr ............. C12Q 1/04
435/304.2
5,976,824 A 11/1999 Gordon
(Continued)

FOREIGN PATENT DOCUMENTS

CA 2 264 206 A1 2/1998
DE 198 06 780 C1 7/1999
(Continued)

OTHER PUBLICATIONS

Jan. 26, 2018 International Search Report issued in International Patent Application No. PCT/FR2017/052755.
(Continued)

*Primary Examiner* — Nathan A Bowers
(74) *Attorney, Agent, or Firm* — Oliff PLC

(57) ABSTRACT

A device and method preparing a sample that may contain a target microorganism, includes: placing the sample in a container including: a device for the capture and/or concentration of a target microorganism or of a protein therefrom, including a capture and/or concentration support; a receptacle including; inlet and fluid guides, a device controlling the sample volume transferred from the fluid guide to the capture and/or concentration device through the inlet orifice, an outlet orifice; the capture/concentration device being attached to a wall of the receptacle; generating a displace-
(Continued)

ment of all or part of the sample to the fluid guide and a defined sample volume from the fluid guide to the capture and/or concentration device, capturing and/or concentrating, on the capture and/or concentration support, the target microorganism or a protein from the microorganism, the volume of sample crossing the capture and/or concentration support then exiting again through the outlet orifice.

19 Claims, 6 Drawing Sheets

(51) Int. Cl.
*C12M 1/00* (2006.01)
*C12Q 1/24* (2006.01)
*G01N 1/00* (2006.01)
*G01N 1/40* (2006.01)

(52) U.S. Cl.
CPC .............. *C12Q 1/24* (2013.01); *G01N 1/40* (2013.01); *G01N 1/405* (2013.01); *C12M 47/06* (2013.01); *G01N 1/4005* (2013.01)

(56) References Cited

U.S. PATENT DOCUMENTS

| | | | |
|---|---|---|---|
| 2011/0003380 A1* | 1/2011 | Miltenyi | A61M 1/3693 |
| | | | 435/308.1 |
| 2011/0207209 A1* | 8/2011 | Hammons | C12M 23/42 |
| | | | 435/303.1 |
| 2011/0294205 A1 | 12/2011 | Hukari et al. | |
| 2013/0071872 A1 | 3/2013 | Ho et al. | |
| 2018/0128723 A1* | 5/2018 | Ryu | B01L 3/502753 |

FOREIGN PATENT DOCUMENTS

FR 2 853 326 A1 10/2004
WO 2014/072438 A1 5/2014

OTHER PUBLICATIONS

Jan. 26, 2018 Written Opinion of the International Searching Authority issued in International Patent Application No. PCT/FR2017/052755.

\* cited by examiner

METHOD AND DEVICE FOR PREPARING SAMPLES

TECHNICAL FIELD

The present invention relates, in general, to the preparation of a sample for the purposes of capturing and concentrating a microorganism or a protein from said microorganism. The field of application of the invention is that of microbiology and more particularly that of industrial microbiology.

PRIOR ART

The raw products used and the converted products sold by the food-processing industry (meat products, dairy products, seafood products, plants, etc.), and also the pharmaceutical and cosmetic products and the water intended for drinking, are subjected to numerous microbiological tests in order to ensure that they are innocuous (absence of pathogenic bacteria or of degradation, absence of bacteria which are markers of contamination dangerous to the health, absence of toxins).

The microbiological analysis of these products requires precise techniques in which the time required to obtain the result must be as short as possible.

In the medical field, it is necessary to predict and diagnose infectious risk: the faster and more accurate the diagnosis, the more effective the treatment of the diseases and the more the risk of transmission is minimized. The approach is similar for animal health in the veterinary field.

In the food sector, the problem is identical. However, it distinguishes:
 pathogenic microorganisms (such as *Salmonella* or the *E. coli* strain O157:H7) and toxins thereof, the investigation of which applies to raw materials, intermediate products and final products sold,
 nonpathogenic microorganisms, used as quality indicators for the production process, from the raw materials to the final products, throughout the chain,
 bacteria of technological interest, such as ferments,
 contamination marker microorganisms.

The rapid and precise detection of presumed contaminants (within food batches) makes it possible to control them and to thus quickly initiate corrective actions.

Technically, microbiological analysis generally implements one or more pre-enrichment and/or enrichment phases, one or more detection phases, and one or more microorganism counting phases. For specific applications, such as food-processing microbiological testing, a confirmation phase may also be required, in order to meet the standards in force in this field.

The detection phase is historically based on the growing (culture) of microorganisms on essentially agar media, and through the demonstration of the metabolic characteristics of the microorganisms being sought. Specific enzymatic substrates are conventionally used. These substrates may be compounds used in bacterial metabolism and which result in a modification of the medium, said modification being detected by indicators (pH variation, reduction, precipitation, etc.). In other cases, these enzymatic substrates are composed of two portions, a first portion specific for the enzymatic activity to be revealed, also known as target portion, and a second portion which acts as a marker, also known as marker portion, generally consisting of a chromophore or a fluorophore. Through the choice of these substrates, depending on whether or not there is a reaction, it is possible to characterize the nature of a microorganism or to distinguish various groups of microorganisms. Thus, the appearance or disappearance of a coloration or of a fluorescence will be the signature of a genus or of a type of microorganism. In this regard, the use of chromogenic media makes it possible to simultaneously detect and identify the microorganisms being sought. It simplifies the process and substantially decreases the time taken to obtain the result. By way of a concrete example, mention will be made of the applicant's ChromID® media. These chromogenic media are based on the detection of metabolic characteristics specific for the microorganisms being sought, for instance beta-glucuronidase enzymatic activity for *Escherichia coli*.

Immunoassays constitute another of the technologies used for the detection test. They make use of the immunogenic characteristics of the microorganisms being sought. Mention may be made, in a nonexhaustive manner, of the competitive ELISA ("Enzyme Linked Immuno Sorbent Assay") or sandwich ELISA techniques.

Finally, molecular biology techniques, based on the genomic characteristics of the microorganisms being sought, are also carried out for detecting and identifying target microorganisms. These molecular biology techniques offer extremely advantageous perspectives. By way of example, mention will be made of conventional amplification techniques such as PCR (Polymerase Chain Reaction) and NASBA (Nucleic Acid Sequence Based Amplification), which can be coupled to real-time detection techniques known to those skilled in the art.

The confirmation phase, for its part, is sometimes required in order to confirm the presence of the pathogen being sought, when the result of the methods developed above is positive. This means that an additional test and the use of a detection agent other than that used during the first analysis are required. The techniques described above are used at will for the confirmation.

The complete and precise identification of a microorganism in a sample therefore requires the linking together of several steps: enrichment, detection and, where appropriate, confirmation. Standardization of the tests routinely used has made it possible to automate the detection methods which, however, remain lengthy to carry out. One drawback of the conventional analysis methods used in the prior art lies in the fact that the enrichment, detection and, where appropriate, confirmation steps are carried out sequentially and require a large number of time-consuming manipulations, thus impacting on the time required to produce the results.

As previously indicated, the detection phase is generally preceded by at least one pre-enrichment and/or enrichment phase (more generally referred to as enrichment phase or step for the purposes of the present application). The latter is essential in so far as, at the current time, there is no method for detecting a target microorganism in a biological sample, present in a minimal amount, for example of the order of a few cells in the sample, without using a prior enrichment step. This enrichment phase requires the use of selective or nonselective (depending on the desired objective) culture media which have the objective of promoting the growth of the target microorganisms in the biological or environmental samples, while at the same time limiting the growth of the non-target flora. The culture media are frequently used in containers of sterile plastic bag type, in which they are brought into contact with the food or environmental samples, for the purposes of resuspending and enriching the microorganisms being sought. As mentioned above, this enrichment phase is necessary in particular in order to reveal the presence of at least one target microorganism in a very variable and possibly very large amount of sample, for example from 25 grams (g) to 375 g diluted in a volume of culture medium of between 225 and 3375 milliliters (ml). At the end of this enrichment step, an aliquot (generally having a volume of between 5 microliters (µl) and 5 ml) is conventionally taken in order to carry out the step of detecting the target microorganisms. However, in this aliquot, it is necessary to have a sufficient amount of target microorganisms to be sure of their systematic detection.

Thus, at the end of incubation and despite the use of selective media, the concentration of target microorganisms remains insufficient in certain cases and/or the concentration of secondary flora remains too high to perform an effective detection of the target microorganisms. In this configuration, those skilled in the art generally have recourse to methods for treating the sample which have the objective of increasing the ratio between the concentration of target microorganisms and the concentration of secondary flora. For example, after enrichment, a fraction of the sample (preferentially between 1 and 10 ml) is treated by means of an immunoconcentration method using magnetic beads functionalized with antibodies specific for the target microorganisms.

However, this method for treating the sample is limited by the small volume of the aliquot used. It is painstaking since it is completely manual and also has a risk of user contamination since the sample, potentially containing pathogenic agents, is handled after enrichment.

In addition, the enrichment step requires not only an ad-hoc culture medium, but also an incubation of the whole mixture formed at least by the biological sample and the culture medium at an optimum temperature so as to allow growth of the target microorganism(s).

The incubation is generally carried out at a temperature ranging from 25 to 45° C. for a predetermined period of time (for example from 6 h to 48 h). However, during this incubation period, no additional action is carried out on the sample. No advantage of this period of time is then obtained, it is in a way "lost". In point of fact, this goes against the problem presented above, aimed at developing a precise and rapid analysis technique. Indeed, during this enrichment step, the sample is immobilized in an incubator without means of intervention since this step is generally carried out overnight.

In view of the sum of the problems developed above, one of the objectives of the present invention aims to improve the capture and/or concentration of the target microorganisms (of interest) or of the proteins from said microorganisms by increasing the contact time with a capture and/or concentration support.

Another objective of the present invention is to control the volume of sample in contact with the binding partners of the capture support, the contact time of the sample with these binding partners and therefore the flow rate of the sample through the capture support. This new technique thus makes it possible to optimize the reaction conditions for the binding partners with the microorganisms or the proteins from these microorganisms contained in the sample.

Another objective of the present invention aims to provide a (preferably automated) treatment of the sample on a large volume of sample and not only on an aliquot, said treatment consisting in capturing and concentrating the target microorganisms (of interest) or the proteins from said microorganisms with a view to improving the sensitivity and the specificity of the detection method used post-treatment.

The objective of the invention is also to exploit/optimize the incubation time during the phase of enrichment of the biological sample by carrying out, during the period of incubation/enrichment and of growth of the microorganisms, a capture and/or a concentration of the target microorganisms present in the sample (preferably in an automated manner).

Another objective of the present invention is to provide a method which makes it possible to increase the rate of analysis of the samples and/or to decrease the total time required for the analysis of the biological sample.

Another objective of the present invention aims to limit the manipulations of the sample contained in the container, consequently limiting the risks of contamination, either of the personnel handling the sample, or of the sample itself. In this regard, a subject of the present invention is the development of an automated or semi-automated method for preparing a sample.

Another objective of the present invention is to improve the traceability of the analysis owing to the drastic reduction in the sample handling steps.

Other objectives will emerge on reading the present application.

The present invention thus aims to achieve all or some of the abovementioned objectives.

SUMMARY OF THE INVENTION

The container used for the purposes of the present invention comprises:
   a device for the capture and/or concentration of a microorganism or of a protein from said microorganism, comprising a capture and/or concentration support,
   a receptacle comprising at least two walls, at least one of which is flexible, capable of receiving at least one sample that may contain at least one target microorganism, said receptacle comprising
      an inlet orifice made through one of said walls and allowing the sample contained in the receptacle to pass to the capture and/or concentration device,
      an inlet fluid guide, capable of containing a defined sample volume and making it possible to guide said sample volume to said inlet orifice,
      at least one means for controlling the flow rate of sample transferred from the fluid guide to the capture and/or concentration device through said inlet orifice,
      an outlet orifice made through one of said walls allowing the sample to pass from the capture and/or concentration device to the receptacle,
   said capture and/or concentration device being attached to a wall of the receptacle.

According to the present invention, the container comprises a device for the capture and/or concentration of a microorganism or of a protein from said microorganism, comprising a capture and/or concentration support. Advantageously, the capture and/or concentration device is partly placed right next to the outer face of one of said walls of the receptacle. More preferentially, the receptacle comprises at least two leaktight connectors fitted to the inlet and outlet orifices of the receptacle. The leaktight connectors then prevent the sample from spilling out of the container and thus from contaminating the surroundings or the technician handling the sample.

In one preferred embodiment, the capture/concentration device can be in the form of a cartridge attached to the receptacle. Preferentially, the capture and/or concentration device can be detached from the wall of said receptacle.

In one particular embodiment, the capture/concentration device is composed of two parts:
- a first part corresponding to a cartridge holder that can be attached to the wall of the receptacle,
- and a second part corresponding to the cartridge comprising the capture support.

According to this particular embodiment, the present invention relates to a container as described above, characterized in that the device for the capture and/or concentration of a microorganism or of a protein from said microorganism comprises
- a cartridge holder comprising:
  - at least one insertion means allowing a cartridge to be inserted into the cartridge holder,
  - at least one first intake duct allowing the entry of a liquid sample; the first intake duct being linked to an intake pathway of the cartridge when the cartridge holder and the cartridge are positioned according to a "capture/concentration" fluid path,
  - at least one second intake duct allowing the entry of a washing liquid and/or of a lysis liquid and/or of an elution liquid; the second intake duct being linked to an intake pathway of the cartridge when the cartridge holder and the cartridge are positioned according to a "lysis and/or washing and/or elution" fluid path,
  - at least one discharge duct allowing the exit of the liquid sample and/or the washing, lysis or elution liquid; the discharge duct being linked to the discharge pathway of the cartridge;
- a cartridge comprising:
  - at least one insertion means allowing the cartridge to be inserted in at least two different positions, a first position according to a "capture/concentration" fluid path and a second position according to a "lysis and/or washing and/or elution" fluid path,
  - a reaction module comprising
    - at least one intake pathway for the liquid sample and/or the washing and/or lysis and/or elution liquid allowing it (them) to enter the module,
    - at least one discharge pathway for the liquid sample and/or the washing and/or lysis and/or elution liquid allowing it (them) to be discharged to the cartridge holder and then to the container,
    - a capture and/or concentration support placed between the intake pathway and the discharge pathway such that all or some of the sample or of the liquids passes through it.

The cartridge may comprise a lid and a bottom assembled by clip-fastening, adhesive bonding, welding, snap-riveting, riveting, crimping, or any other means allowing a reliable and strong assembly. The leaktightness between the lid and the bottom of the cartridge can be produced by simple adhesive bonding. It can also be produced by adding an adhesive, silicone or mastic between the ad-hoc faces of the lid and the bottom of the cartridge. It can also be produced by means of a joint and counter-joint.

The capture support is placed inside the reaction module of the cartridge.

The cartridge and the cartridge holder comprise an insertion means. The term "insertion means" is intended to mean any means which makes it possible to guide the cartridge in the cartridge holder. This may for example be runners. Preferentially, the insertion means contains an error-proofing feature, for example an asymmetrical runner, making it possible to guide the cartridge in the cartridge holder in a single direction.

Preferentially, the device is attached to a wall of a receptacle suitable for receiving a sample. Preferentially, the cartridge holder and/or the cartridge can be detached from the wall of said receptacle.

In one particular embodiment, a base is placed right next to the internal face of the wall of the receptacle and comprises
- at least one channel for intake of the liquid sample, fluidically linked to the sample intake pathway of the cartridge via the first intake duct of the cartridge holder,
- at least one channel for discharge of the liquid sample and/or washing and/or lysis, fluidically linked to the discharge pathway of the cartridge via the discharge duct of the cartridge holder.

The cartridge, the cartridge holder and the base may consist of a plastic, for example they may be injection-molded in a polymer of the class of polyolefins or polyamides or polyesters (nonlimiting). Certain biobased materials may also be envisioned. According to one preferential embodiment, the base is connected to a fluid guide which allows the sample contained in the receptacle to reach the intake channel of the base.

The container used for the purposes of the present invention comprises a receptacle which is open or closed (for example hermetically closed or sealed closed) comprising at least two walls, at least one of which is flexible. According to one preferred embodiment, the receptacle is a bag which has a flexible envelope of the homogenization bag type. Preferably, at least one wall of the receptacle is transparent in order to be able to see the volume occupied by the liquid inside the receptacle.

According to the present invention, the receptacle comprises an inlet fluid guide, capable of containing a defined volume of sample and making it possible to guide said volume of sample to said inlet orifice.

The fluid guide may consist of any means which makes it possible to guide the biological sample contained in the receptacle to the inlet orifice of the capture/concentration device. According to one particularly preferred embodiment, the fluid guide is elastic and intended to be pressed. It may be a tube made of silicone material for example.

According to another embodiment, the fluid guide is an internal bag, of the receptacle, which is intended to be pressed. Preferentially, at least one portion of the internal bag is a portion of the flexible wall of the receptacle.

The fluid guide may consist of any means which makes it possible to guide the biological sample contained in the receptacle to the intake channel of the base. According to one particularly preferred embodiment, the fluid guide is elastic and is intended to be pressed. It may be a tube made of silicone material for example.

According to the invention, the receptacle may comprise an outlet fluid guide allowing fluid communication between the outlet orifice of the capture and/or concentration device and the receptacle.

The fluid guide may optionally be equipped with a vent system which prevents the walls of the receptacle from sticking to one another and obstructing the passage to the capture and/or concentration device.

According to the invention, the receptacle comprises a means for controlling the volume of sample transferred from the fluid guide to the capture and/or concentration device through said inlet orifice. In one preferred embodiment, the means for controlling the volume is a section having a given diameter of the fluid guide and the size (the length) of the fluid guide.

According to one embodiment of the invention, the receptacle may comprise a compartment used to receive the filtrate of the sample, a filter separating said receptacle into two compartments, one used to receive the sample, the other used to receive the filtered sample.

According to another embodiment, the fluid guide comprises a filter which prevents the capture support from being obstructed with certain samples.

If the upper part of the container is considered to be the "top" part and the lower part of this container is considered to be the "bottom" part, the inlet orifice may be located in the bottom part and the outlet orifice in the top part. In that case, schematically, the sample circulates through the capture/concentration support from bottom to top. In another embodiment, the inlet orifice may be located in the top part and the outlet orifice in the bottom part. In that case, the sample will circulate through the capture/concentration support by gravity from top to bottom.

In the particular embodiment of the container comprising a cartridge and a cartridge holder, if the upper part of the container is considered to be the "top" part and the lower part of the container is considered to be the "bottom" part, the intake pathway and the first intake duct for the sample may be located in the bottom part and the discharge pathway and the discharge duct may be located in the top part. In that case, schematically, the sample circulates through the capture/concentration support from bottom to top. In another embodiment, the intake pathway and the first intake duct may be located in the top part and the discharge pathway and the discharge duct may be located in the bottom part. In that case, the sample will circulate through the capture/concentration support by gravity from top to bottom.

In one particular embodiment, the capture and/or concentration device comprises a means for recovering the nucleic acids once the microorganisms have been lysed by the lysis liquid, said recovering means being able to be placed in fluid communication with the second intake duct of the cartridge holder.

According to the present invention, the sample may be of various origins, for example of food, environmental, veterinary or clinical origin. Among the samples of food origin, mention may be made, nonexhaustively, of a milk product (yogurt, cheese, etc.), meat, fish, egg, fruit, vegetable, water or drink (milk, fruit juice, soda, etc.) sample. Of course, these samples of food origin may also originate from more elaborate sources or dishes or from non-transformed or partially transformed raw materials. Finally, a food sample may come from an animal feed, such as oilcakes or animal meals. By way of example of samples, mention should also be made of samples associated with the environment, such as specimens taken from a surface, water, air, etc.

The samples of clinical origin may correspond to specimens taken from biological fluids (whole blood, serum, plasma, urine, cerebrospinal fluid, etc.), from stools, specimens taken from the nose, throat, skin, wounds, organs, tissues or isolated cells. This list is obviously not exhaustive.

In general, the term "sample" refers to a portion or to an amount (more particularly a small portion or a small amount) taken from one or more entities for the purposes of analysis. This sample may optionally have undergone a prior treatment, involving for example mixing, diluting or else milling steps, in particular if the starting entity is in the solid state, or else pre-enrichment or enrichment steps by bringing into contact with a culture medium. It may also be filtered beforehand or in the same receptacle or the same capture/concentration device. The sample is therefore in liquid form during the method according to the present invention.

The sample may of course, in addition to the culture medium, comprise additional elements, such as vitamins or other nutritive elements that are of use for the culture of microorganisms, selective agents, specific substrates and other elements well known to those skilled in the art.

The sample analyzed is, in general, capable of—or suspected of—containing at least one target microorganism. In most cases, the latter is a pathogenic microorganism (such as *Salmonella*) that it is advisable to check for health reasons.

The term "microorganism" has the same meaning as that generally accepted in microbiology and comprises in particular a gram-positive or gram-negative bacteria, yeasts, molds and, more generally, single-cell organisms invisible to the naked eye, which can be handled and multiplied in the laboratory.

According to one preferred embodiment, the microorganism(s) to be detected is (are) bacteria, for example enterobacteria such as *E. coli*.

The present invention also applies to the capture and/or concentration of protein(s) from said microorganism, such as toxins. By way of illustration, mention may be made of the detection of the toxins secreted by *Staphylococcus aureus*.

Advantageously, the sample comprises at least one culture medium which allows the growth of microorganisms, and in particular of the target microorganism(s). The term "culture medium" is intended to mean a medium comprising all the elements required for the survival and/or growth of microorganisms, and in particular of the microorganisms being sought (for example buffered peptone water). The culture medium may contain optional additives, for example: peptones, one or more growth factors, carbohydrates, one or more selective agents, buffers, one or more gelling agents, one or more vitamins, etc. This culture medium may be in ready-to-use liquid or gelled form, namely ready to be inoculated into a tube, into a flask or onto a petri dish. The expression "culture medium" of course encompasses enrichment media and broths.

The term "capture and/or concentration support" is intended to mean any support which makes it possible to bind the microorganism or the protein from said microorganism being sought and to make sure that it is in a sufficient concentration for the purposes of the subsequent analysis steps. The "capture and/or concentration support" will also be mentioned without distinction as "capture/concentration support".

Preferentially, the "capture and/or concentration support" is chosen from particulate supports and one-piece supports. The capture/concentration support may be particles. Preferentially, the capture and/or concentration support is a porous capture and/or concentration support. It is preferably a porous membrane.

Advantageously, the capture and/or concentration support is functionalized with at least one binding partner specific for the target microorganism or for a protein from said microorganism.

According to one preferred embodiment, the specific binding partner is selected from the group comprising antibodies, Fab fragments, Fab' fragments, recombinant or non-recombinant phage proteins, phages or any other ligand well known to those skilled in the art. The analysis can be carried out in situ using the capture and concentration support. The presence of the target microorganisms on the capture and concentration support can be revealed by means of any appropriate revealing system, that is to say capable of allowing the detection of the target microorganism(s). The term "revealing system" is intended to mean any molecule capable of coupling with the microorganisms or the binding partners for said microorganisms while making it possible, by virtue of their transduction (fluorescence, coloring, radioactivity, etc.) properties, to reveal the presence of said microorganisms. This revealing of the presence of the target microorganisms may in particular be obtained by visualization (with the naked eye) or optical reading (via an optical reading device of camera type) of a coloration (such as a red coloration due to the reduction of TTC to formazan by the microorganisms) or of a fluorescence on all or part of the capture support.

In a nonlimiting manner, the analysis may be carried out by any detection means, it being possible for said detection means to be selected from optical detection means, electrical (in particular electrochemical) detection means, acoustic detection means, thermal detection means, mechanical detection means and magnetic detection means.

A subject of the present invention is also the use of the container for capturing and concentrating a microorganism or a protein from said microorganism included in a sample.

In one particular embodiment, the container may be placed in a device comprising at least one location for receiving said container, said device comprising
- at least one means for applying pressure on the fluid guide in order to trap, in the fluid guide, a given sample volume,
- and at least one displacement means for generating the displacement of the sample contained in the receptacle to the fluid guide and/or from the fluid guide to the capture/concentration support.

Thus, the displacement of the sample can be performed manually or mechanically. Such a device is described in patent application WO 2014/072438 filed by the applicant. It may be a paddle (or arm) device, said paddles compressing the flexible-walled receptacle (for example made of plastic of PVC, polyester, polyester type). This device allows optimal control of the flow rate of circulation of the sample in the capture/concentration support. The means for applying pressure may, for its part, be any means which makes it possible to pinch the fluid guide, preventing the sample outside the fluid guide to enter into the fluid guide.

A subject of the present invention is also the development of a method for preparing a sample that may contain at least one target microorganism, comprising essentially the following steps:
a) placing said sample in a container comprising:
  a device for the capture and/or concentration of a target microorganism or of a protein from said microorganism, comprising a capture and/or concentration support;
  a receptacle with at least two walls, at least one of which is flexible, capable of receiving said sample that may contain at least one target microorganism, said receptacle comprising
    an inlet orifice made through one of said walls and allowing the liquid sample contained in the receptacle to pass to the capture and/or concentration device,
    an inlet fluid guide, capable of containing a defined sample volume and making it possible to guide said sample volume to the inlet orifice,
    at least one means for controlling the volume of sample transferred from the fluid guide to the capture and/or concentration device through said inlet orifice,
    an outlet orifice made through one of said walls allowing the sample to pass from the capture and/or concentration device to the receptacle,
    said capture/concentration device being attached to a wall of the receptacle;
b) generating a displacement of all or part of the sample to the fluid guide,
c) generating a displacement of a defined volume of the sample from the fluid guide to the capture and/or concentration device through the inlet orifice,
d) capturing and/or concentrating, on the capture and/or concentration support, said target microorganism or a protein from said target microorganism contained in the sample, said volume of sample crossing the capture and/or concentration support and then exiting again through the outlet orifice of the receptacle.

A subject of the present invention is also the development of a method for preparing a sample that may contain at least one target microorganism as described above, characterized in that the capture and/or concentration device comprises
  a cartridge holder comprising:
    at least one insertion means allowing a cartridge to be inserted into the cartridge holder,
    at least one first intake duct allowing the entry of a liquid sample; the first intake duct being linked to the intake pathway of the cartridge when the cartridge holder and the cartridge are positioned according to a "capture/concentration" fluid path,
    at least one second intake duct allowing the entry of a washing liquid and/or of a lysis liquid and/or of an elution liquid; the second intake duct being linked to an intake pathway of the cartridge when the cartridge holder and the cartridge are positioned according to a "lysis and/or washing and/or elution" fluid path,
    at least one discharge duct allowing the exit of the liquid sample and/or of the washing or lysis liquid to the container; the discharge duct being linked to the discharge pathway of the cartridge;
  a cartridge comprising:
    at least one insertion means allowing the cartridge to be inserted in at least two different positions, a first position according to a "capture/concentration" fluid path and a second position according to a "lysis and/or washing and/or elution" fluid path;
  a reaction module comprising
    at least one intake pathway for the liquid sample and/or for the washing and/or lysis and/or elution liquid allowing it (them) to enter the module,
    at least one discharge pathway for the liquid sample and/or for the washing and/or lysis and/or elution liquid allowing it (them) to be discharged to the cartridge holder and then to the container,
    a capture and/or concentration support placed between the intake pathway and the discharge pathway such that all or some of the sample or of the liquids crosses it.

Preferably, the displacement of the sample to the capture and/or concentration device is carried out mechanically and repeatedly.

The recirculation of the sample through the capture support makes it possible to increase the microorganism contact time with the capture/concentration support and therefore to increase the probability of the microorganism encountering the capture/concentration support.

According to the present invention, the sample may optionally have undergone a prior treatment, involving for example pre-enrichment or enrichment steps by bringing into contact with a culture medium. This step of bringing the sample into contact with a culture medium can also be carried out in the container according to the invention.

Thus, advantageously, said method comprises a step of incubating said sample at a temperature and for a period of time sufficient to allow the growth of said at least one target microorganism, the incubation step being carried out before step a) or during all or part of steps a) to d). In this context, the incubation time may be optimized by choosing to carry out the capture/concentration during the incubation.

With regards to the incubation step, those skilled in the art will know, based on their experience, on their general knowledge and/or on the bibliographical data at their disposal, to adjust the temperature and the period of time required to allow sufficient growth of the target microorganism, as a function of type of target microorganism being sought. By way of indication, and as mentioned in the preamble of the present application, the incubation is in general carried out at a temperature ranging from 25 to 45° C. for a predetermined period of time (for example from 6 h to 48 h).

The displacement of all or part of the sample to the fluid guide and then to the capture and/or concentration device through the inlet orifice can be obtained by any means known by those skilled in the art. The fluid guide(s) allow(s) the content to come into contact with the inlet orifice while at the same time preventing the content from coming into contact with the outlet orifice if it has not passed through the capture and concentration device.

In particular, this displacement can be generated by applying a force or a set of forces on the container or else upon changing the balance of the forces being applied to the container. Thus, for example, if the container is held at two points by two holding forces and if one of the two forces ceases, the container will tilt and the level of the container will vary, at the level of at least one part of the internal surface of the container, from the resting level to a level located above the latter and will possibly be brought into contact with the means intended to create the inlet orifice via the fluid guide. The displacement of the content can also be obtained by applying a force or a system of forces inside the receptacle, for example by inflating and deflating an inflatable flexible bag (such as an inflatable balloon or an inflatable coil) placed in the chamber of the receptacle. Advantageously, steps b) and c) are carried out using a device comprising a displacement means and a pressure means as described above, in order to exert a pressure on the fluid guide and to allow a given volume of the sample to be brought into contact with the capture and/or concentration support. Such a device is described in patent application WO 2014/072438 deposited by the applicant. It may be a paddle (or arm) device, said paddles compressing the flexible-walled receptacle (for example made of plastic of PVC, polyethylene or polyester type).

According to one embodiment, the capture and/or concentration support is a porous membrane. Preferentially, the circulation is carried out by tangential flow through the membrane, which has the advantage of increasing the contact time between the microorganism and the capture support.

Advantageously, all or part of the sample contained in the receptacle circulates through the capture/concentration support at a flow rate of between 0.5 ml/min per $cm^2$ of support and 5 ml/min per $cm^2$ of support, said support being porous and having a developed surface area of at least 20 $cm^2$.

The present invention has the advantage of allowing the capture and the revelation of the presence of a target microorganism in a very variable and possibly very large amount of sample, for example from 25 grams (g) to 375 g diluted in a volume of culture medium of between 225 and 3375 ml. Thus, the volume of the sample that may pass through the capture/concentration device is between 10 ml and 5000 ml, preferentially between 50 ml and 4000 ml, more preferentially between 200 and 3500 ml, even more preferentially between 225 and 3375 ml.

This method advantageously makes it possible to use a large starting volume for carrying out the capture/concentration, which makes it possible to increase the probability of the target microorganism (or the protein from this microorganism) encountering the capture/concentration support. Preferentially, at least 10 ml of the sample contained in the receptacle circulates through the capture and/or concentration support, preferentially at least 50 ml.

Thus, the method for preparing a sample, according to the invention, is a method for the capture/concentration of at least one target microorganism of a sample that may contain said at least one target microorganism. It is a method intended to allow the capture/concentration of at least one target microorganism, preferably in the presence of at least one enrichment broth/culture medium. When it is suspected that the microorganism(s) being sought is (are) present in minimal amount, for example about a few cells, in the sample, this method allows said at least one target microorganism to be present at the end of the method according to the invention at a concentration such that the user can optionally systematically or virtually systematically detect it by using conventional detection methods (culture on agar medium, immunoassays, molecular biology techniques, etc.).

A subject of the present invention is thus the development of a method for preparing a sample that may contain at least one target microorganism, comprising the following steps:

a) placing said sample in a container comprising a cartridge holder and a cartridge as described above, said cartridge holder and said cartridge being positioned according to a "capture/concentration" fluid path, b) generating a displacement of all or part of the sample to the fluid guide, c) generating a displacement of a defined volume of the sample from the fluid guide to the capture and/or concentration device through the inlet orifice, d) capturing and/or concentrating, on the capture and/or concentration support, said target microorganism or a protein from said target microorganism contained in the sample, said volume of sample crossing the capture and/or concentration support and then exiting again through the outlet orifice of the receptacle.

In one particular embodiment, the method for preparing a sample according to the present invention also comprises one or more step(s) of washing with a washing liquid dispensed in the second intake duct of the cartridge holder, the cartridge being placed according to a "lysis and/or washing and/or elution" fluid path.

A translational movement of the cartridge in the cartridge holder by following the runners makes it possible to pass from a "capture/concentration" fluid path to a "lysis and/or washing and/or elution" fluid path.

In another particular embodiment, the method for preparing a sample according to the present invention also comprises one or more step(s) of lysis with a lysis liquid dispensed in the second intake duct of the cartridge holder, the cartridge being placed according to a "lysis and/or washing and/or elution" fluid path.

In another particular embodiment, the method for preparing a sample according to the present invention comprises one or more step(s) of elution with an elution liquid dispensed in the second intake duct of the cartridge holder, said cartridge being placed according to a "lysis and/or washing and/or elution" fluid path.

In another particular embodiment, the method for preparing a sample according to the present invention comprises a subsequent step of suctioning the liquid of interest containing the nucleic acids of said microorganisms released during the lysis.

This suctioning step can be carried out using a syringe (said syringe possibly being used to inject the washing/lysis solution) or else a duct, a Vacutainer®, a PSIpette or else a peristaltic pump, connected to the second intake duct of the cartridge holder.

In another embodiment, the preparation method comprises a subsequent step of decontaminating with a decontaminant dispensed in the second intake duct of the cartridge holder, the cartridge being placed according to a "lysis and/or washing and/or elution" fluid path.

Advantageously, the method according to the invention makes it possible to efficiently capture and concentrate a target microorganism of a biological sample while at the same time limiting the operations of handling the sample contained in the receptacle, as a result limiting the risks of contamination, either of the personnel handling the sample, or of the sample itself.

According to one embodiment, the method according to the invention comprises a subsequent step of analyzing said capture support and concentrating by visual reading, optical reading or any other means. Thus, this method makes it possible to analyze said target microorganism(s) and/or all or some of their properties. The analysis may in particular consist of a method of direct detection—and where appropriate identification—of said microorganism(s) or of a method of indirect detection—and where appropriate identification—, for example linked to the detection of nucleotide and/or protein information specific for a type of microorganism to be detected and/or identified. This indirect detection and/or identification can also result from the detection of proteins which specifically bind to bacteriophage proteins specific for said microorganism(s) to be detected. The presence of a target microorganism can also be detected by resistance to a given antibiotic or to a set of antibiotics, the profile of resistance to this or these antibiotic(s) being, in this case, characteristic of the microorganism(s) to be detected. The direct or indirect detection can be carried out in situ on the capture support after, for example, addition of a revealing system.

In one particular embodiment, the analysis of said capture and concentration support is carried out after detachment of the capture/concentration device and/or of said capture/concentration support from the receptacle.

Thus, the analysis of the capture/concentration support can also be carried out ex situ by transferring the capture/concentration device and/or support into an analysis device. In one preferred embodiment, the microorganisms coupled to the capture/concentration support are lysed in order to recover the nucleic acids, then analyzed by means of an amplification method such as PCR.

The method according to the present invention also makes it possible to carry out sterility controls, in particular in food and environmental specimens. To do this, generic means for detection of microorganisms, such as capture supports functionalized with generic binding partners of anti-gram−, anti-gram+, etc., type are used as analysis means. The type of analysis carried out with the method of the invention can therefore not only be qualitative (detection and identification of specific microorganism(s)), but can also be quantitative or semi-quantitative.

BRIEF DESCRIPTION OF THE DRAWINGS

The invention, its functionality, its applications and also its advantages will be understood more clearly on reading the present description, given with reference to the figures, in which.

DETAILED DESCRIPTION OF THE CONTAINER AND OF THE METHOD ACCORDING TO THE INVENTION

The aim of the detailed description hereinafter is to disclose the invention sufficiently clearly and completely, in particular by means of examples and of references to figures, but it should not in any way be regarded as limiting the scope of the protection to the particular embodiments which are the subject of said examples and figures.

Figure 1:
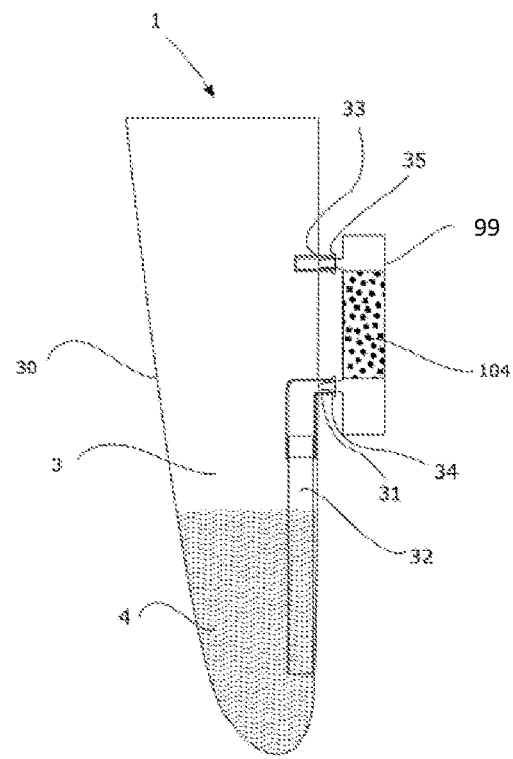
FIG. 1 represents diagrammatically a container according to the invention, the capture/concentration device being outside the receptacle.

The device for preparing a sample (1), as represented in FIG. 1, in accordance with a first embodiment, represents a receptacle (3) comprising a capture/concentration device (99) attached to the external wall, which can be detached.

This receptacle (3) comprises a flexible wall (30), which is optionally transparent, through which an inlet orifice (31) and an outlet orifice (33) have been made.

Inside the receptacle, an inlet fluid guide (32) makes it possible to guide the sample (4) from the receptacle to the inlet orifice (31) and then to the capture and/or concentration device (99).

The sample crosses the capture/concentration support (101) and then passes through the outlet orifice (33) made through the flexible wall (30) to the inside of the receptacle.

The capture and/or concentration device comprises at least two connectors (34) and (35) fitted to the inlet and outlet orifices of the receptacle. These two connectors are resistant to pressure and fitted in a leaktight manner, preventing the sample from spilling out the container and thus from contaminating the surroundings or the technician handling the sample.

Figure 2:
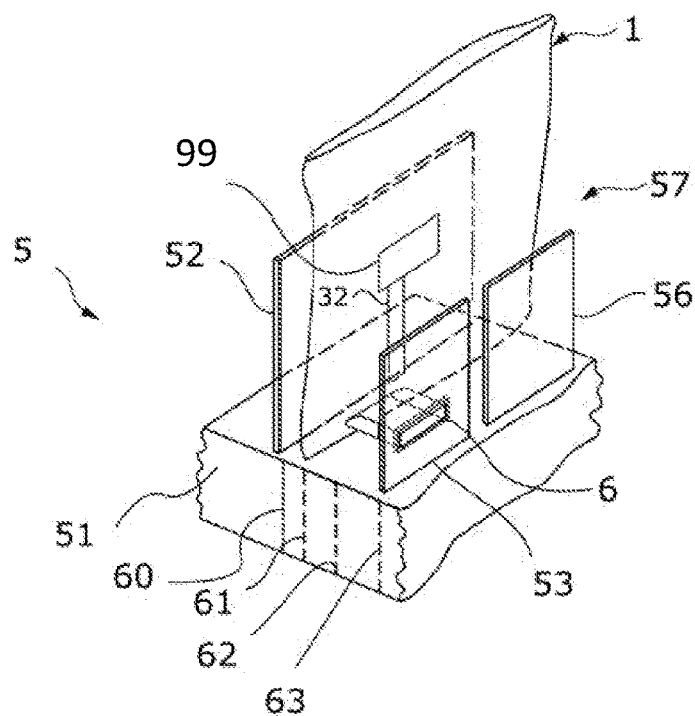
FIG. 2 represents diagrammatically a device with a container, a means for applying pressure on the fluid guide in order to trap a given volume of sample in the fluid guide, and a displacement means for generating the displacement of the sample contained in the fluid guide to the capture and/or concentration device, FIGS. 3, 4 and 5 aim to illustrate the device as represented in FIG. 2 during the various steps of bringing the displacement means and the pressuring means into contact with the container, thus generating the displacement of the sample contained in the fluid guide to the capture and/or concentration device.

FIG. 2 represents a device (5) comprising a container (1) positioned in the device (5), in a location (57) provided for this purpose.

This location (57) is delimited on one side by the fixed wall (52) and on the other by displacement means represented by a first removable arm and a second removable arm (similar to two paddles) (53) and (56). One of the roles of the arms is to homogenize, to blend the sample. The arms can move countercurrent and/or in phase opposition (phase half-cycle).

The pressuring means (6) is linked to one of the paddles in order to exert a pressure on the fluid guide (32), through the flexible wall of the receptacle. The receptacle and the fluid guide come into abutment against the fixed wall. The pressuring means, by crushing the fluid guide at the distal end of the inlet orifice against the fixed wall, traps a given volume of sample in the fluid guide. The fluid guide is an elastic tube. It may be a silicone tube of small thickness so as to reduce the crushing force, but with elastic properties which allow it to return to its initial geometry. The means for controlling the volume corresponds to the diameter and to the length of the tube. The diameter and the length of the tube must be defined with the aim of having an optimized volume of sample passing through the capture support. The diameter and the length of the tube will also be defined as a function of the pressure exerted on the tube in order to establish an optimized flow rate through the capture support.

The displacement means (53) and (56) also generate the displacement of the sample contained in the fluid guide to the capture and/or concentration device. It should be noted that the pressuring means (6) can be replaced with applicators of varied shapes, provided that said applicators are capable of exerting a certain force making it possible to press the fluid guide against the fixed wall; the fluid communication of the sample from outside the guide to inside the guide is thus blocked. The pressure means is a protuberance attached to the paddle (53).

In the interests of clarity, FIG. 2 represents only one portion of the device according to the invention. The device (5) is provided with a base (51) onto which a wall (52) has been attached. The two paddles (53) and (56) are removable relative to the base (51). The movement of said arms (53) and (56) relative to the base (51) can be generated by any suitable means, such as an electric motor.

Figure 3:
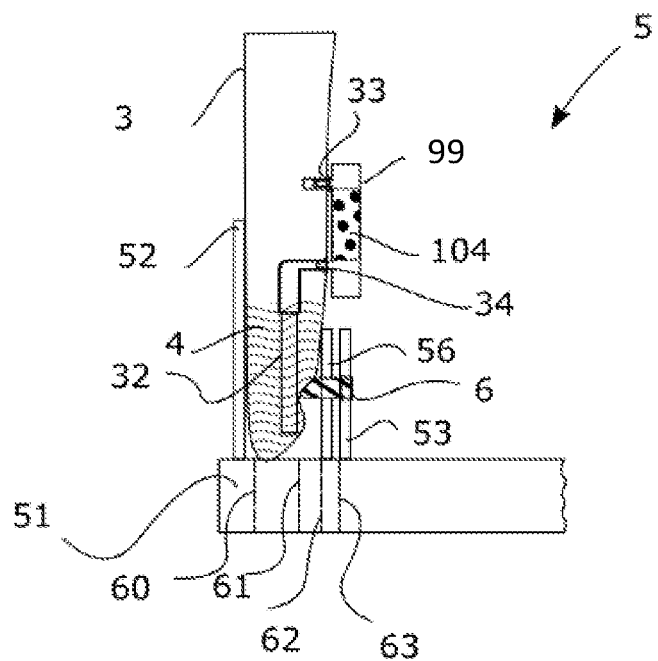
Figure 4:
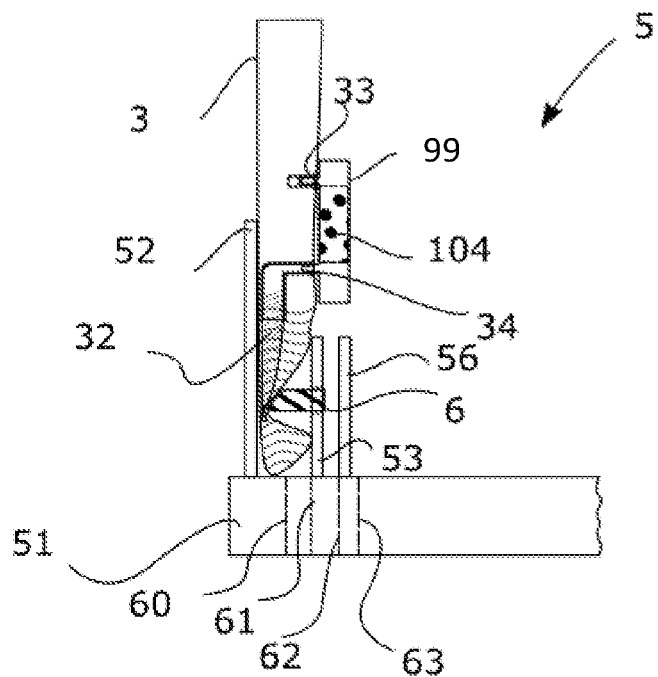
Figure 5:
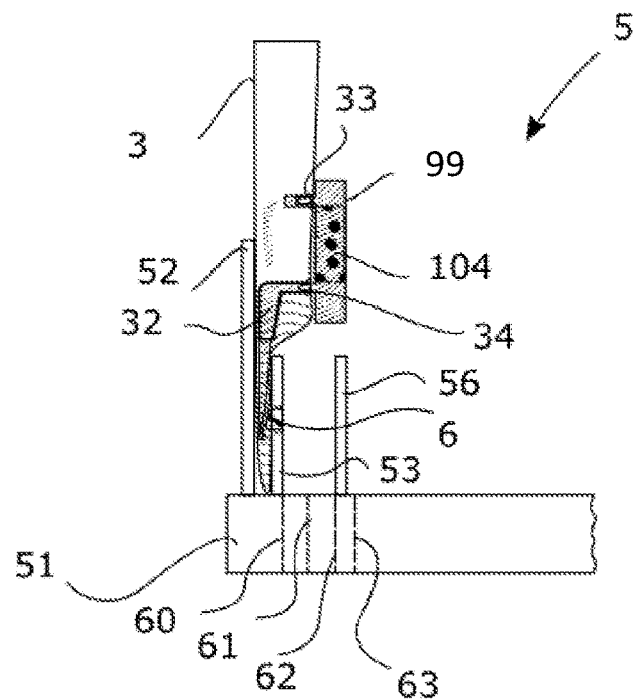

FIGS. 3 to 5 represent the device (5) during operation at various steps.

In FIG. 3, the arm (53) is in a position distant from the container, indicated by means of the line (63) and the arm (56) is in a closer position indicated by means of the line (62). The distance between the arm (53) and the container does not allow the pressuring means (66) to press the fluid guide.

In FIG. 4, the arm (53) moves to a position close to the container, indicated by means of the line (61), the force exerted by the pressuring means (6) on the fluid guide (32) pushed against the fixed wall (52) leads to pinching of the fluid guide, trapping a volume of sample within it.

In FIG. 5, the arm (53) moves to a position even closer to the container, indicated by means of the line (60), the pressing means (6) retracts and the arm (53) in contact with the container brings about the displacement of the volume of sample contained in the fluid guide to the capture and/or concentration device.

Thus, the capture and/or concentration device is brought into contact with the microorganisms from the biological sample to be analyzed and, if the target bacteria are present among said microorganisms, said bacteria bind to their specific binding partner present in said capture and/or concentration device, for example to a functionalized antibody. The target bacteria are then (immuno) concentrated in the capture and/or concentration device and can be identified in situ, for example by means of immunodetection techniques well known to those skilled in the art, implementing revealing systems that are also well known to those skilled in the art. According to one variant, the identification step is carried out outside the container, for example using an automated device of VIDAS® type.

The biological sample (4) may be any sample for which the user wishes to test for the presence of microorganisms of interest. As indicated above, the sample may be of food, environmental or clinical origin (nonexhaustive list) and the microorganisms sought may be pathogenic microorganisms, for example of the *salmonella* or *E. coli* type.

When the container (1) is positioned in the location (57), the assembly formed by the device (5) and the container (1) may, for example, be incubated inside an incubator (not represented). The conditions may be optimized inside said incubator so as to allow the growth of the microorganisms being sought. Characteristics, such as the temperature can also be adjusted in order to be optimal for promoting the growth of the target microorganisms. When the assembly formed from the device (5) and the connector (1), positioned in the location (57), is introduced into the incubator, the operation of the arms (53) and (56) can be activated.

The arms (53) and (56) can move from their first position (63) to their second position (62) (and vice versa). This movement makes it possible to exert a force on the outside surface of the flexible wall of the container (1) and to thus impose on said container (1) a deformation of this flexible wall. At this stage, the arms (53) and (56) can serve to homogenize the content of the container (1).

The arms (53) and (56) can be periodically displaced. The frequency can be chosen and adapted to the type of sample and/or to the type of culture medium that are present inside the container (1).

At a chosen time during the incubation or after the incubation, the arm to which the pressuring means (6) is attached can move into a closer position, as explained above. Indeed, one advantageous embodiment is to delay the bringing of the sample into contact with the capture and/or concentration device without however waiting for the end of the incubation.

This incubation phase extends, for example, over 24 hours during which the concentration of target microorganisms will gradually increase. In the first ten hours for example, the concentration of target microorganisms is too low to interact with the capture and/or concentration support. Thus, during these first ten hours, and as indicated above, it is preferable to keep the capture and/or concentration device away from the assembly composed of the sample and the culture medium in order to preserve its integrity and to prevent deterioration of the capacities of said support owing to the nonspecific compounds contained in the sample. After ten hours, the capture and concentration support (104) is brought into contact with the sample (4) through the action of the pressuring means on the fluid guide and of the displacement means which push the sample toward the capture device.

The sample moves into the capture support according to a tangential strain before exiting again via the outlet orifice (33) in the receptacle (3). The pressuring means and the displacement means have moved away from the container in order to allow the fluid guide to return to its initial shape. The cycle can recommence, the pressuring means can again pinch the fluid guide and the displacement means can displace the volume of sample trapped in the fluid guide to the capture device. The repeated circulation of the sample through the capture support makes it possible to increase the efficiency of the capture of the target microorganisms.

In the case where the detection is carried out directly on the capture/concentration support, the technician can read the result of the analysis on the capture/concentration support through the capture/concentration device (99).

Figure 6:
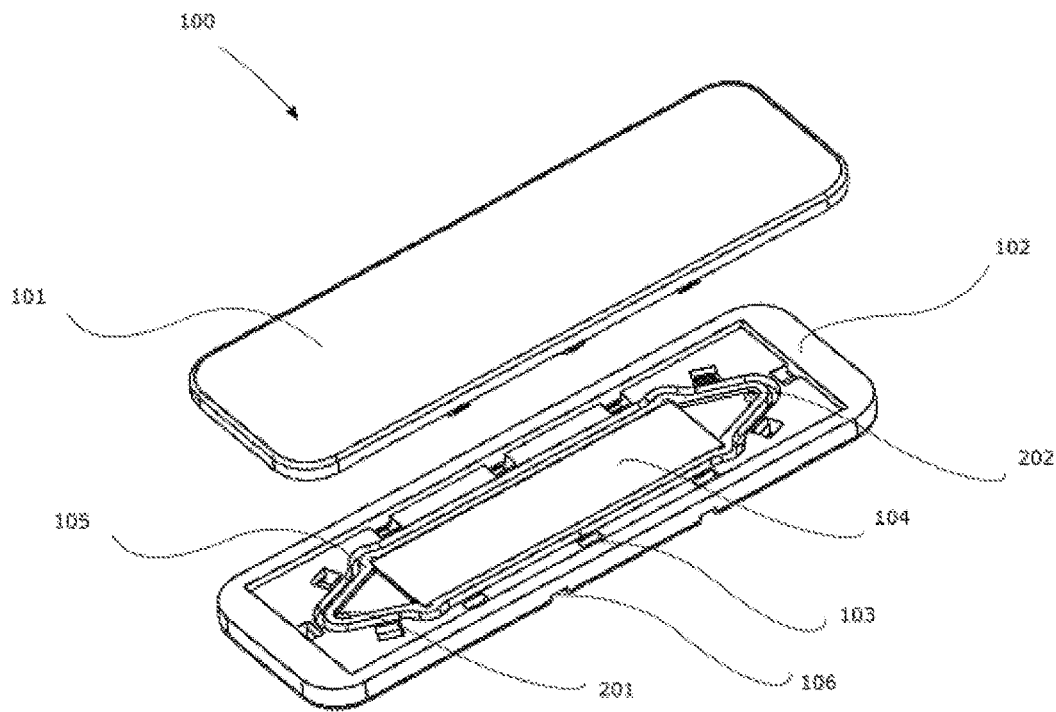
FIG. 6 represents a cartridge according to the invention, the cartridge being open.

Detailed Description of One Particular Embodiment of the Capture/Concentration Device The cartridge (100) as represented in FIG. 6 comprises a lid (101) and a bottom (102) assembled by means of clips (103) which ensure the leaktightness. The capture support (104) is placed inside the reaction module (105) of the cartridge. The capture support is a membrane.

The cartridge comprises:
an intake pathway (201) for the liquid sample and/or the washing liquid and/or the lysis liquid allowing it (them) to enter the module,
a discharge pathway (202) for the liquid sample and/or the washing liquid and/or the lysis liquid and/or the elution liquid.

The capture and/or concentration support (104) is placed between the intake pathway (201) and the discharge pathway (202) such that all or part of the sample or of the liquids crosses it.

Figure 7:
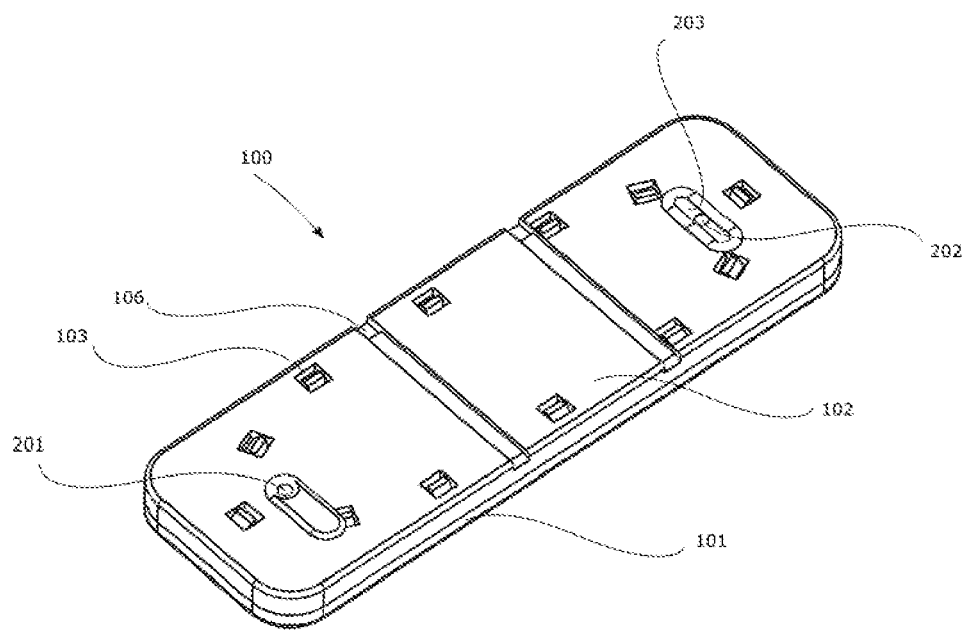
FIG. 7 illustrates a cartridge according to the invention, the cartridge being closed.

FIG. 7 is a view from below of the cartridge represented in FIG. 6. The cartridge (100) is in the closed position, the bottom (102) and the lid (101) are assembled by means of clips (103).

The external face of the bottom (102) comprises runners (106) which serve as an insertion means allowing the cartridge to be inserted into a cartridge holder.

The runners can also act as an error-proofing feature.

The cartridge comprises:
an intake pathway (201) for the liquid sample and/or the washing liquid and/or the lysis liquid allowing it (them) to enter the module,
a discharge pathway (202) for the liquid sample and/or the washing liquid and/or the lysis liquid and/or the elution liquid. An oblong boss (203) makes it possible to enlarge the discharge pathway.

The capture and/or concentration support (104) (not visible in FIG. 2) is placed inside the cartridge between the intake pathway (201) and the discharge pathway (202) such that all or part of the sample or of the liquids crosses it.

Figure 8:
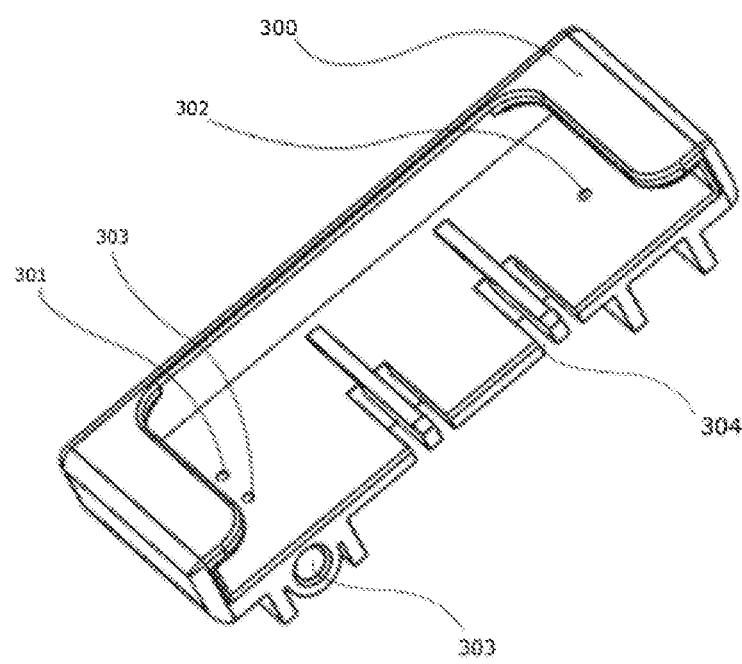
FIG. 8 represents a cartridge holder according to the invention.

The cartridge holder (300) as represented in FIG. 8 comprises
a first intake duct (301) allowing a liquid sample to enter,
a second intake duct (303) allowing a washing liquid and/or a lysis liquid and/or an elution liquid to enter,
a discharge duct (302) allowing the liquid sample and/or the washing or lysis liquid to exit,
an insertion means (304) allowing the cartridge to be inserted into the cartridge holder.

The insertion means of the cartridge holder can also act as an error-proofing feature and prevents accidental withdrawal. It is represented here by runners (304).

The cartridge holder (300) is intended to be placed right next to the external face of the wall of the receptacle.

Figure 9:
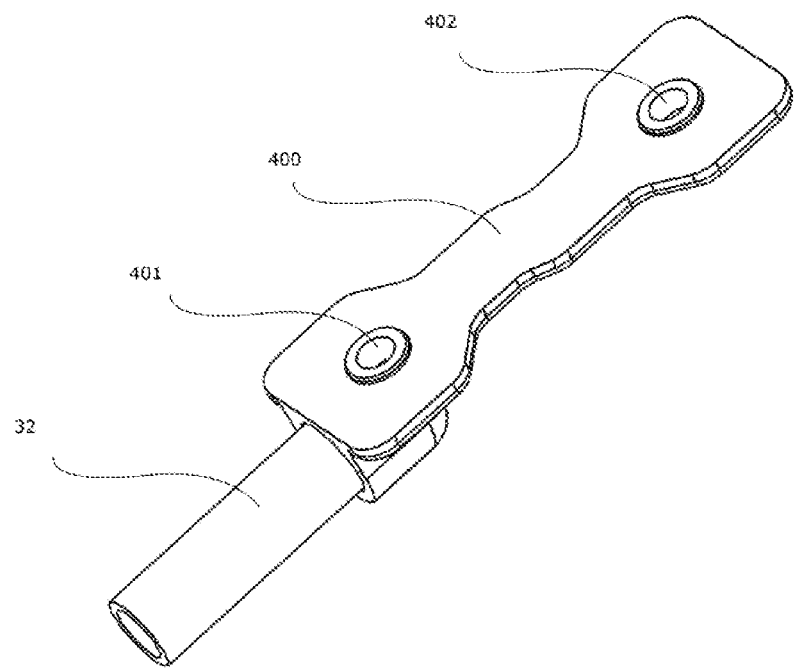
FIG. 9 shows a base and a fluid guide according to the invention.

The base (400) as represented in FIG. 9 is intended to be placed right next to the internal face of the wall of the receptacle.

It comprises:
at least one channel for intake (401) of the liquid sample, fluidically linked to the sample intake pathway of the cartridge (201, FIG. 7) via the first intake duct of the cartridge holder (301, FIG. 8),
at least one channel for discharge (402) of the liquid sample and/or washing and/or lysis, fluidically linked to the discharge pathway of the cartridge (202, FIG. 7) via the discharge duct of the cartridge holder (302, FIG. 8).

The base (400) is connected to a fluid guide (32) allowing the sample contained in the receptacle to reach the intake channel of the base (401).

Figure 10:
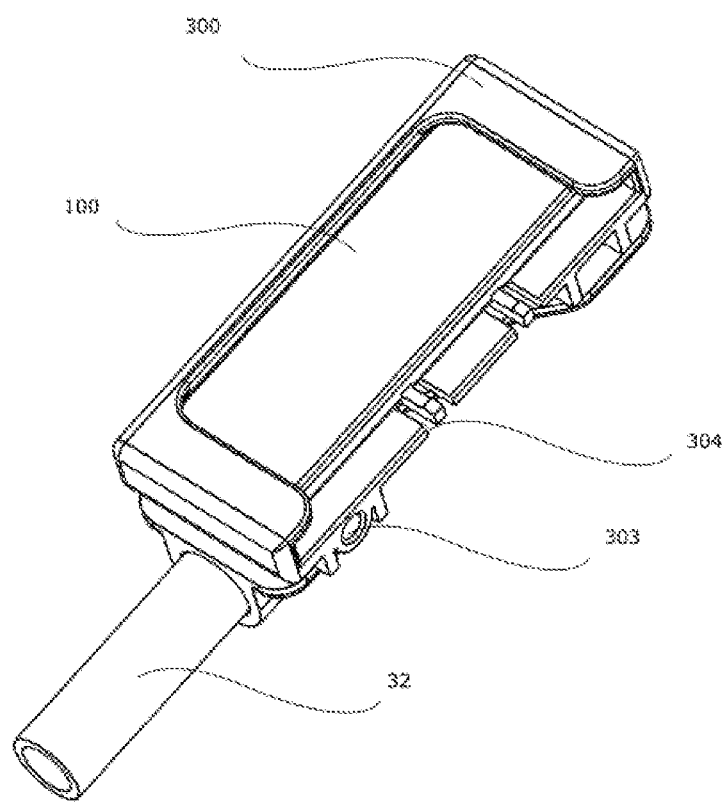
FIG. 10 represents a cartridge inserted into a cartridge holder according to a "capture/concentration" fluid path, the first intake duct of the cartridge holder being fluidically linked to the intake pathway of the cartridge, the discharge duct of the cartridge holder being linked to the discharge pathway of the cartridge, thus allowing the liquid sample to enter the reaction module and to exit again therefrom.

FIG. 10 shows the cartridge (100) placed in the cartridge holder (300) according to a "capture/concentration" fluid path. The intake pathway (201) (represented in FIG. 7) of the cartridge is fluidly linked to the first intake duct (301) (represented in FIG. 8) of the cartridge holder. The discharge pathway (209) (represented in FIG. 7) of the cartridge is linked to the discharge duct of the cartridge holder (302) (represented in FIG. 8), thus allowing the liquid sample to enter the reaction module (105) (FIG. 6) and to exit again therefrom.

A translational movement of the cartridge in the cartridge holder by following the runners (304) makes it possible to move from a "capture/concentration" fluid path to a "lysis and/or washing and/or elution" fluid path.

Figure 11:
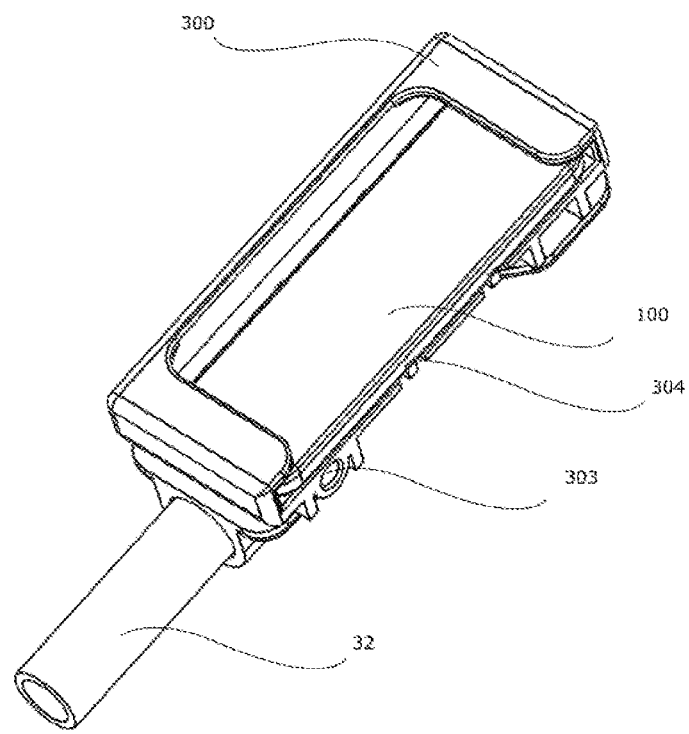
FIG. 11 represents a cartridge inserted into a cartridge holder according to a "lysis and/or washing and/or elution" fluid path, the second intake duct of the cartridge holder being fluidly linked to the intake pathway of the cartridge, the discharge duct of the cartridge holder being linked to the discharge pathway of the cartridge, thus allowing the lysis and/or washing liquid to enter the reaction module and to exit again therefrom.

FIG. 11 shows the cartridge (100) placed in the cartridge holder (300) according to a "lysis and/or washing and/or elution" fluid path. The intake pathway (201) (represented in FIG. 7) of the cartridge is fluidly linked to the second intake duct (303) (represented in FIG. 8) of the cartridge holder. The discharge pathway (302) (represented in FIG. 7) of the cartridge is linked to the discharge duct (202) (represented in FIG. 3) of the cartridge holder, thus allowing the lysis and/or washing and/or elution liquid to enter the reaction module and to exit again therefrom.

Whatever the fluid path chosen, the discharge pathway (202) (represented in FIG. 7) of the cartridge is linked to the discharge duct (302) (represented in FIG. 8) of the cartridge holder by virtue of the presence of an oblong boss (203) (represented in FIG. 7) on the cartridge.

Figure 12:
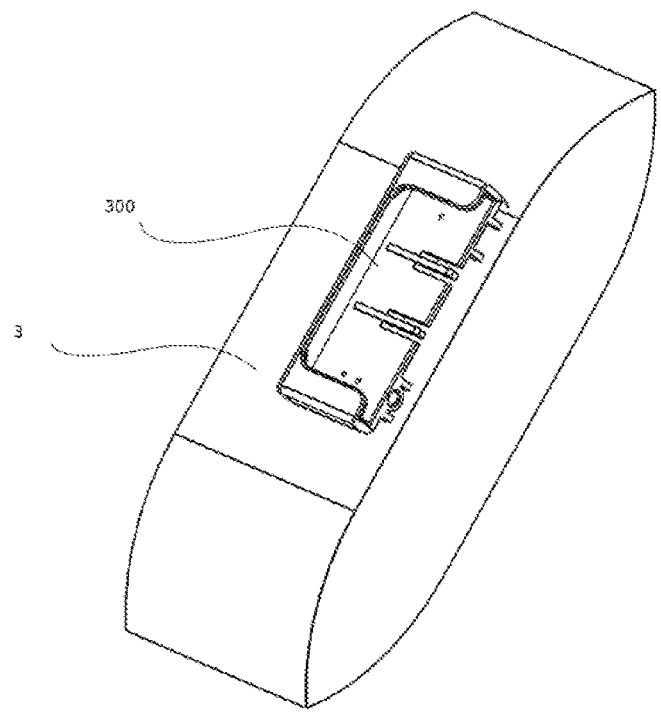
FIG. 12 is a diagrammatic illustration of a cartridge holder attached to the external wall of a receptacle.

According to one embodiment, the cartridge holder (300) is attached to the external face of the wall of the receptacle (3) as represented in FIG. 12. The cartridge can insert into the cartridge holder.

The receptacle can contain a fluid guide which makes it possible to guide the sample from the receptacle to the intake channel of the base, then the first intake duct of the cartridge holder, then the intake pathway of the cartridge.

The sample crosses the capture/concentration support and then passes through the discharge pathway of the cartridge, the discharge duct of the cartridge holder and the discharge channel of the base in order to once again enter the receptacle.

Thus, the capture and/or concentration device is brought into contact with the microorganisms from the biological sample to be analyzed and, if the target bacteria are present among said microorganisms, the said bacteria bind to their specific binding partner present in said capture and/or concentration device, for example to a functionalized antibody.

The sample passes into the capture support according to a tangential flow before exiting again via the discharge pathway in the receptacle.

The repeated circulation of the sample through the pature and/or concentration support makes it possible to increase the efficiency of the capture of the target microorganisms.

The functionality of the invention is illustrated with the (nonlimiting) example presented below.

Example 1

Capture/Concentration Efficiency of the Device According to the Present Invention Materials:
Salmonella Derby strain ref 0904089
Matrix: Minced beef containing 15% fat (Tendre et Plus brand name)
Material: biosensor: functionalized 550 μm membranes (Reemay 2040)
qPCR: GeneUP Salmonella kit (bioMérieux Cat. No. 414150)
10 mM TRIS buffer+0.05% Tween 20
XT1 and XT2 reagent of the Adiafood extraction kit (Cat. No. ADIF9988)
Dry bath for 1.5 ml Eppendorf tube, adjusted to 120° C.
Tween 80
Buffered Peptone Water (BPW) 3 L (bioMérieux Cat. 42629)

Protocol for Functionalizing the Capture Support (Membrane):

The capture support is made of polyester, sold by the company PGI (Cat. No. Reemay 2040). The product is further cut into 4 cm$^2$ (1 cm×4 cm) lamellae.
The support is immersed at 37° C. overnight in a solution of biotinylated BSA (Bovine Serum Albumin) at 5 μg/ml;
The support is then immersed at 37° C. for two hours in a solution of streptavidin at 10 μg/ml;
The support is then immersed for two hours at 37° C. in a solution of specific binding partners (1 μg/ml to 40 μg/ml; the specific binding partner being an anti-Salmonella recombinant phage protein).

The sensitized support thus produced can be used for the detection of the microorganisms or stored at 2-8° C. with a view to a subsequent use.

Preparation of the Assay:

Preparation of the food sample: 375 g of food sample (minced beef containing 15% fat) are weighed in the plastic bag containing the present invention, then 1000 ml of enrichment medium (BPW) and 5 ml of Tween 80 are added. The plastic bag is directly incubated, at 39° C., in the device described in patent application WO 2014/072438 filed by the applicant, implementing gentle homogenization of the sample for five hours of incubation.

Programming of the Homogenization Cycle of the Device:
Lateral transfer mode
Speed: 20 mm/s
Displacement: 35 to 12 mm for the two paddles.

In a device according to the invention as described in FIG. 1, a membrane functionalized with the anti-Salmonella phage protein (SLM membrane) is provided as capture support (Bagflow sample called B+).

An SLM membrane is also immersed. It will thus be in "dipping" mode.

In another identical device, one membrane functionalized with the anti-E. coli 0157 phage protein (ECO membrane called B−) is provided as capture support and acts as a negative control. An ECO membrane is also immersed as nonspecific binding control. It will thus be "dipping" mode.

Preparation of the Bacterial Strain:

Using the Salmonella Derby strain, prepare a suspension at 0.6 McF and then perform successive dilutions in 9 ml trypsone salt tubes (Cat. No. AEB111499) until the $10^3$ CFU/ml dilution is reached. Perform an inoculum control with 100 μl of the $10^3$ CFU/ml dilution plated out on TSA agar (Cat. No. 43011).

Inoculate the plastic bags with the Salmonella Derby strain at 20 CFU/ml, i.e. 200 μl of the $10^5$ CFU/ml dilution.

The bags are homogenized for 5 min (the time for the strain to be uniformly distributed in the bag) before starting the capture cycle.

For the device of the present invention, the circulation sequence lasts 30 min at 2 ml/min, i.e. 60 ml of sample across the capture device.

For the support in dipping mode, the contact time is 30 min with stirring.

Treatment of the Capture Supports after 30 Min of Capture:
Washing of the membranes with 10 mM Tris buffer+ 0.05% Tween 20 by dipping in a pill bottle for the "dipping" membranes and, for the devices, with 3 ml of buffer connected to the device via a syringe.
After the washing, place the membranes in Eppendorf tubes and centrifuge for 5 seconds in order to discharge the residual volume of washing buffer.
Add 100 μl of the extraction kit to each of the membranes.
Incubate for 20 minutes at 42° C.
Centrifuge the membranes for 5 seconds in order to recover the supernatant containing the bacterial DNA.
Incubate at 100° C. for 5 minutes in accordance with the instructions per use of the extraction kit.

In parallel, the food sample pre-enriched for five hours is divided up into 5 aliquots of 9 ml. The aliquots are artificially contaminated with the Salmonella strain at a concentration ranging from $10^4$ to $10^7$ CFU/ml. This range makes it possible to compare the gain in sensitivity between the present invention and the existing method.

GeneUP BioFire Protocol:
Resuspend the PCR reagent with 45 μl of reconstituting buffer.
Vortex for a long time and then centrifuge in order to recover all the liquid.
Place 5 μl of reagent in each of the wells.
Add 5 μl of lysed sample.
Insert the stoppers.
Agitate rapidly and centrifuge the plate.
Launch the qPCR.

Results:

Inoculum control of the suspension at 100 CFU/ml theoretical: 90 CFU/ml qPCR Results:

| Sample | | GENE UP | |
|---|---|---|---|
| | *Salmonella* concentration (CFU/ml) | qPCR GeneUp(Ct) | Interpretation |
| B+ | 20 | 29.7 | + |
| B+ | 20 | 30.6 | + |
| B − (ECO membrane) | 20 | — | − |
| D+ | 20 | 33.3 | + |
| D − (ECO membrane) | 20 | — | − |
| PE $10^4$ | 10 000 | — | − |
| PE $10^5$ | 100 000 | 34.3 | + |
| PE $10^6$ | 1 000 000 | 33.0 | + |
| PE $10^7$ | 10 000 000 | 31.1 | + |

The samples subjected to the method according to the invention (B+) exhibit a capture/concentration yield that is higher by one log compared with the dipping sample.

Indeed, a difference of 3 Ct is observed between the results (B+) and dipping (T+). It is thus demonstrated that circulating the sample through the mesh of the membrane improves the probabilities of capture, between the phage proteins and the bacteria of interest.

The GeneUp qPCR reference method gives a positive result starting from $10^5$ CFU/ml. The capture/concentration method thus makes it possible to gain a minimum of 3 log of sensitivity over the detection method.

CONCLUSION

This example shows the significant gain in the capture/concentration device according to the present invention, compared with simple dipping of the membrane in the sample. The limit of detection of the method (capture+lysis+qPCR) is clearly close to 20 CFU/ml, which makes it possible to considerably reduce the enrichment time and thus the analysis time. Indeed, this level of detection makes it possible to give a positive response to a sample of 375 g of food matrix contaminated at 1 CFU, in less than 5 h of incubation.

The invention claimed is:

1. A method for preparing a sample containing microorganisms, comprising the following steps:

a) placing the sample in a container comprising:
   a capture and/or concentration device designed for capturing and/or concentrating a target microorganism or a protein from the target microorganism, comprising a capture and/or concentration support that is functionalized with a binding partner that is specific for the target microorganism or the protein from the target microorganism; and
   a receptacle with at least two walls, at least one of which is flexible, capable of receiving the sample, the receptacle comprising
      an inlet orifice made through one of the walls and allowing the sample contained in the receptacle to pass to the capture and/or concentration device,
      an inlet fluid guide, capable of containing a defined volume of sample and making it possible to guide the volume of sample to the inlet orifice,
      an outlet orifice made through one of the walls allowing the volume of sample to pass from the capture and/or concentration device to the receptacle, and
      at least one means for controlling the volume of sample transferred from the fluid guide to the capture and/or concentration device through the inlet orifice,
   wherein the capture and/or concentration device is attached to at least one of the walls of the receptacle such that the capture and/or concentration device is detachable from the receptacle after being attached;

b) generating a displacement of all or part of the sample to provide the volume of sample to the fluid guide, c) generating a displacement of the volume of sample from the fluid guide to the capture and/or concentration device through the inlet orifice, and d) capturing and/or concentrating, on the capture and/or concentration support, the target microorganism or the protein from the target microorganism when present among the microorganisms contained in the sample, the volume of sample crossing the capture and/or concentration support and then exiting through the outlet orifice of the receptacle, wherein:

the volume of sample is added back to the sample remaining in the receptacle after exiting through the outlet orifice of the receptacle;

steps (b)-(d) are repeatedly performed so as to recirculate additional volumes of sample through the capture and/or concentration support; and the capture and/or concentration device comprises (i) a cartridge comprising a reaction module that includes the capture and/or concentration support and (ii) a cartridge holder in which the cartridge is removably inserted, the cartridge comprising:
   at least one insertion means allowing the cartridge to be inserted in at least two different positions, a first position according to a capture/concentration fluid path and a second position according to a lysis and/or washing and/or elution fluid path, and
   the reaction module comprising:
      at least one intake pathway for the volume of sample and/or washing and/or lysis and/or elution liquid allowing it (them) to enter the reaction module,
      at least one discharge pathway for the volume of sample and/or washing and/or lysis and/or elution liquid allowing it (them) to be discharged, and
      the capture and/or concentration support, which is placed between the intake pathway and the discharge pathway such that the volume of sample or the liquid crosses it, and the cartridge holder comprising:
   at least one cartridge insertion means allowing the cartridge to be removably inserted into the cartridge holder,
   at least one first intake duct allowing entry of the volume of sample; the first intake duct being linked to the intake pathway of the cartridge when the cartridge holder and the cartridge are positioned according to the capture/concentration fluid path,
   at least one second intake duct allowing entry of the washing liquid and/or of the lysis liquid and/or of the elution liquid; the second intake duct being linked to the intake pathway of the cartridge when the cartridge holder and the cartridge are positioned according to the lysis and/or washing and/or elution fluid path, and at least one discharge duct allowing exit of the volume of sample and/or washing liquid and/or lysis liquid to the container; the discharge duct being linked to the discharge pathway of the cartridge.

2. The method as claimed in claim 1, wherein the displacement of the volume of sample to the capture and/or concentration device is carried out mechanically.

3. The method as claimed in claim 1, wherein the sample further comprises a culture medium.

4. The method as claimed in claim 1, further comprising one or more step(s) of washing with the washing liquid dispensed in the second intake duct of the cartridge holder, the cartridge being placed according to the lysis and/or washing and/or elution fluid path.

5. The method as claimed in claim 1, further comprising one or more step(s) of lysis with the lysis liquid dispensed in the second intake duct of the cartridge holder, the cartridge being placed according to the lysis and/or washing and/or elution fluid path.

6. The method as claimed in claim 1, further comprising one or more step(s) of elution with the elution liquid dispensed in the second intake duct of the cartridge holder, the cartridge being placed according to the lysis and/or washing and/or elution fluid path.

7. The method as claimed in claim 1, further comprising a subsequent step of suctioning liquid of interest containing nucleic acids of the microorganisms released during lysis.

8. The method as claimed in claim 1, wherein the capture and/or concentration support is a porous membrane.

9. The method as claimed in claim 1, wherein at least 10 ml of the sample contained in the receptacle circulates through the capture and/or concentration support.

10. The method as claimed in claim 1, wherein all or part of the sample contained in the receptacle circulates through the capture and/or concentration support at a flow rate of between 0.5 ml/min per $cm^2$ of support and 5 ml/min per $cm^2$ of support, the support being porous and having a developed surface area of at least 20 $cm^2$.

11. A method for analyzing a sample containing microorganisms, comprising implementing the method as claimed in claim 1 to prepare the sample, and then analyzing the sample by analyzing the target microorganism or protein from the target microorganism that is captured and/or concentrated on the capture and/or concentration support.

12. A method for preparing a sample containing microorganisms, comprising the following steps:

a) placing the sample in a container comprising:
   a capture and/or concentration device designed for capturing and/or concentrating a target microorganism or a protein from the target microorganism, comprising a capture and/or concentration support; and
   a receptacle with at least two walls, at least one of which is flexible, capable of receiving the sample, the receptacle comprising
      an inlet orifice made through one of the walls and allowing the sample contained in the receptacle to pass to the capture and/or concentration device,
      an inlet fluid guide, capable of containing a defined volume of sample and making it possible to guide the volume of sample to the inlet orifice, and
      an outlet orifice made through one of the walls allowing the volume of sample to pass from the capture and/or concentration device to the receptacle,
   wherein the capture and/or concentration device is attached to at least one of the walls of the receptacle;

b) generating a displacement of all or part of the sample to provide the volume of sample to the fluid guide, c) generating a displacement of the volume of sample from the fluid guide to the capture and/or concentration device through the inlet orifice, and d) capturing and/or concentrating, on the capture and/or concentration support, the target microorganism or the protein from the target microorganism when present among the microorganisms contained in the sample, the volume of sample crossing the capture and/or concentration support and then exiting through the outlet orifice of the receptacle, wherein the capture and/or concentration device comprises
   a cartridge insertable in at least two different positions, a first position according to a capture/concentration fluid path and a second position according to a lysis and/or washing and/or elution fluid path, and
   a reaction module comprising
      at least one intake pathway for the volume of sample and/or washing and/or lysis and/or elution liquid allowing it (them) to enter the module,
      at least one discharge pathway for the volume of sample and/or washing and/or lysis and/or elution liquid allowing it (them) to be discharged, and
      the capture and/or concentration support, which is placed between the intake pathway and the discharge pathway such that the volume of sample or the liquid crosses it, and
   a cartridge holder configured to allow insertion of the cartridge, comprising:
      at least one first intake duct allowing entry of the volume of sample; the first intake duct being linked to the intake pathway of the cartridge when the cartridge holder and the cartridge are positioned according to the capture/concentration fluid path,
      at least one second intake duct allowing entry of the washing liquid and/or of the lysis liquid and/or of the elution liquid; the second intake duct being linked to the intake pathway of the cartridge when the cartridge holder and the cartridge are positioned according to the lysis and/or washing and/or elution fluid path, and
      at least one discharge duct allowing exit of the volume of sample and/or washing liquid and/or lysis liquid to the container; the discharge duct being linked to the discharge pathway of the cartridge.

13. The method as claimed in claim 12, wherein at least 10 ml of the sample contained in the receptacle circulates through the capture and/or concentration support.

14. The method as claimed in claim 12, wherein all or part of the sample contained in the receptacle circulates through the capture and/or concentration support at a flow rate of between 0.5 ml/min per $cm^2$ of support and 5 ml/min per $cm^2$ of support, the support being porous and having a developed surface area of at least 20 $cm^2$.

15. A container comprising:
a receptacle with at least two walls, at least one of which is flexible, capable of receiving a sample containing microorganisms, the receptacle comprising
- an inlet orifice made through one of the walls and allowing the sample contained in the receptacle to pass to a capture and/or concentration device designed for capturing and/or concentrating a target microorganism or a protein from the target microorganism,
- an inlet fluid guide, capable of containing a defined volume of sample and making it possible to guide the volume of sample to the inlet orifice,
- at least one means for controlling the volume of sample transferred from the fluid guide to the capture and/or concentration device through the inlet orifice,
- an outlet orifice made through one of the walls allowing the sample to pass from the capture and/or concentration device to the receptacle, the capture and/or concentration device attached to at least one of the walls of the receptacle, such that the capture and/or concentration device is detachable from the receptacle after being attached, and connected to the inside of the receptacle, the capture and/or concentration device comprising
- a cartridge comprising:
  - at least one insertion means allowing the cartridge to be inserted in at least two different positions, a first position according to a capture/concentration fluid path and a second position according to a lysis and/or washing and/or elution fluid path,
  - a reaction module comprising
    - at least one intake pathway for the volume of sample and/or washing and/or lysis and/or elution liquid allowing it (them) to enter the reaction module,
    - at least one discharge pathway for the volume of sample and/or washing and/or lysis and/or elution liquid allowing it (them) to be discharged, and
    - a capture and/or concentration support that is functionalized with a binding partner that is specific for the target microorganism or the protein from the target microorganism, which is placed between the intake pathway and the discharge pathway such that the volume of sample or the liquid crosses it, and
- a cartridge holder comprising:
  - at least one cartridge insertion means allowing the cartridge to be removably inserted into the cartridge holder,
  - at least one first intake duct allowing entry of the volume of sample contained in the container; the first intake duct being linked to the intake pathway of the cartridge when the cartridge holder and the cartridge are positioned according to the capture/concentration fluid path,
  - at least one second intake duct allowing entry of the washing liquid and/or lysis liquid and/or elution liquid; the second intake duct being linked to the intake pathway of the cartridge when the cartridge holder and the cartridge are positioned according to the lysis and/or washing and/or elution fluid path, and
  - at least one discharge duct allowing exit of the volume of sample and/or washing liquid and/or lysis liquid to the container; the discharge duct being linked to the discharge pathway of the cartridge.

16. The container as claimed in claim 15, wherein a base is placed right next to an internal face of one of the walls of the receptacle and comprising
- at least one intake channel for intake of the volume of sample, fluidly linked to the sample intake pathway of the cartridge via the first intake duct of the cartridge holder, and
- at least one discharge channel for discharge of the volume of sample and/or washing and/or lysis and/or elution liquid, fluidly linked to the discharge pathway of the cartridge via the discharge duct of the cartridge holder.

17. The container as claimed in claim 16, wherein the base is connected to a fluid guide which allows the sample contained in the receptacle to reach the intake channel of the base.

18. The container as claimed in claim 15, wherein the capture and/or concentration support is a porous membrane.

19. The container as claimed in claim 15, wherein the capture and/or concentration device comprises:
- a means for recovering nucleic acids once the microorganisms have been lysed by the lysis liquid, the recovering means being able to be placed in fluid communication with the second intake duct of the cartridge holder.

* * * * *